United States Patent
Merchant et al.

[19]
[11] Patent Number: 5,818,985
[45] Date of Patent: Oct. 6, 1998

[54] OPTICAL OXIMETER PROBE ADAPTER

[75] Inventors: Adnan I. Merchant, Fremont; K. L. Venkatachalam, Palo Alto, both of Calif.

[73] Assignee: Nellcor Puritan Bennett Incorporated, Pleasanton, Calif.

[21] Appl. No.: 575,336

[22] Filed: Dec. 20, 1995

[51] Int. Cl.[6] .............................. G02B 6/35; G01N 33/49
[52] U.S. Cl. .............................. 385/20; 128/633; 356/41; 385/53
[58] Field of Search .................... 356/41; 385/15, 385/16, 20, 21, 22, 53, 75; 128/632, 633, 637

[56] References Cited

U.S. PATENT DOCUMENTS

| | | | |
|---|---|---|---|
| 4,278,327 | 7/1981 | McMahon et al. | 385/20 X |
| 5,249,576 | 10/1993 | Goldberger et al. | 128/632 |
| 5,287,853 | 2/1994 | Vester et al. | 128/633 |
| 5,387,122 | 2/1995 | Goldberger et al. | 439/353 |
| 5,417,207 | 5/1995 | Young et al. | 128/634 |

FOREIGN PATENT DOCUMENTS

WO 82/01948  6/1982  WIPO ............................ G06F 15/04

*Primary Examiner*—John D. Lee
*Attorney, Agent, or Firm*—Townsend and Townsend and Crew LLP

[57] ABSTRACT

The present invention provides an adapter which actively connects a two terminal oximeter probe or monitor to a three terminal monitor or probe. This is done actively, with the alternating drive signals from the oximeter monitor providing a control signal for switching the adapter connections. The adapter connections are preferably made with diodes, transistors, or other active devices.

31 Claims, 9 Drawing Sheets

OPTICAL OXIMETER PROBE ADAPTER

TECHNICAL FIELD

This invention relates in general to optical oximeters and relates more particularly to an adapter that enables an optical oximeter probe, that is designed/configured to be utilized on an associated oximeter monitor, to be used on a different oximeter monitor that utilizes a different probe configuration.

CONVENTION REGARDING REFERENCE NUMERALS

In the figures, each element indicated by a reference numeral will be indicated by the same reference numeral in every figure in which that element appears.

BACKGROUND OF THE INVENTION

Because of the importance of oxygen for healthy human metabolism, it is important to be able to measure the oxygen content of a patient's blood. The monitoring of a patient's arterial hemoglobin oxygen saturation during and after surgery is particularly critical.

Noninvasive oximeters have been developed that direct light through a patient's skin into a region, such as a finger, containing arterial blood. This light typically contains two or more primary wavelengths of light. Examples of such oximeters are disclosed in U.S. Pat. No. 5,209,230 entitled "Adhesive Pulse Oximeter Sensor With Reusable Portion" issued to Swedlow, et al. and in U.S. Pat. No. 4,700,708 entitled "Calibrated Optical Oximeter Probe" issued to New, Jr. et al., both assigned to the assignee of the present invention, the disclosures of which are incorporated herein by reference. The oximeter in the patent by New, Jr. et al. includes a probe that contains a resistor having a resistance that can be measured by a monitor to which the probe is attached. The measured value of this resistance is indicative of the wavelengths of the light directed from the light emitting diodes (LEDs) through the patient's epidermis. The monitor uses this information and the measured intensities of light detected at those wavelengths to calculate the blood arterial oxygen content of the patient. The LEDs are activated in non-overlapping temporal intervals, so that the amount of absorption of light at each of these two wavelengths is measured separately.

Figure 1:
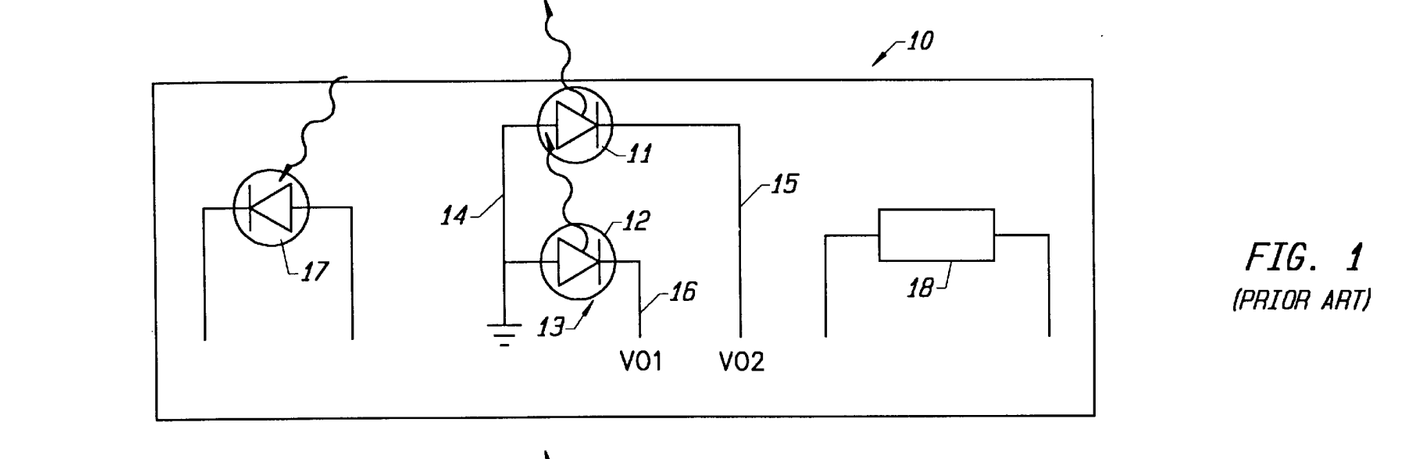
FIG. 1 illustrates a probe with a 3-lead configuration of a pair of LEDs.
Figure 2:
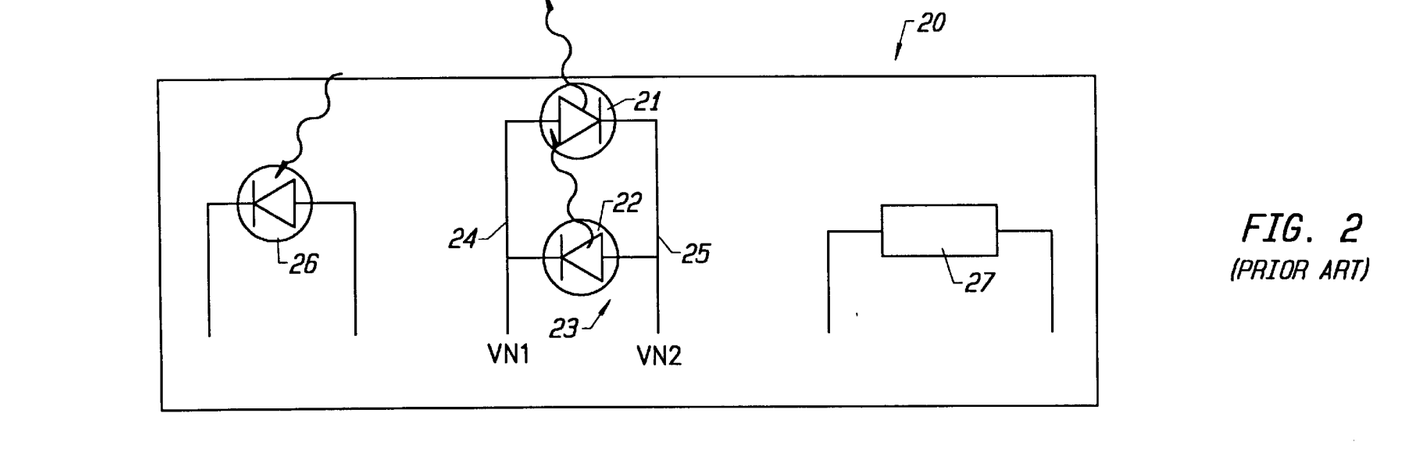
FIG. 2 illustrates a probe with a 2-lead configuration of a pair of LEDs.

Optical probes can be electrically configured in a plurality of ways. U.S. Pat. No. 5,249,576 entitled "Universal Pulse Oximeter Probe" issued to Goldberger, et al., illustrates two configurations of a red light emitting diode (LED) and an infrared LED that emit light into a patient's finger. These two prior art configurations are illustrated in FIGS. 1 and 2. FIG. 1 shows a probe configuration 10 in which a pair of LEDs 11 and 12 are connected in a "3-lead configuration" 13 in which the two LED anodes are connected to a terminal 14 and in which the two LED cathodes are each connected to uniquely associated leads 15 and 16. This probe also includes: a photodetector 17 that detects light emitted from LEDs 11 and 12; and a resistor 18 having a resistance which is indicative of the wavelength of light produced by at least one of LEDs 11 and 12 (alternately, the resistance can indicate other or additional parameters). A probe having a 3-lead configuration of LEDs will be referred to herein as a "3-lead probe" 10. The leads to the LEDs 14, 16, and 15 are indicated as ground, VO1, and VO2, respectively. The VO1 and VO2 designations indicate these are the first and second LED drive voltage leads for oximeters made by other than Nellcor, the assignee of this application. The "O" in the VO1 and VO2 terms is intended to refer to "other." Thus, this probe is sometimes referred to as an "other probe."

In a second embodiment, shown in FIG. 2, two LEDs 21 and 22 are connected in a "2-lead configuration" 23 in which the anode of first LED 21 and the cathode of a second LED 22 are connected to a first lead 24, and the cathode of the first LED 21 and the anode of the second LED 22 are connected to a second lead 25. This probe also includes a photodetector 26 and a resistor 27 (or other type of mechanism which is indicative of the wavelength produced by one or both LEDs, and/or other parameters). A probe having a 2-lead configuration of LEDs will be referred to herein as a "2-lead probe 20". The leads to the LEDs are indicated as VN1, and VN2, corresponding to the Nellcor probe first and second voltage signals. This type of probe is also sometimes referred to as a "Nellcor probe."

An oximeter monitor that is designed to utilize a probe having the 2-lead configuration of LEDs will be referred to herein as an "2-lead -monitor" or "Nellcor oximeter monitor." Similarly, an oximeter monitor that is designed to utilize a probe having the 3-lead configuration of LEDs will be referred to herein as a "3-lead monitor" or "other oximeter monitor."

Some oximeter probes may use one or more additional LEDs. For instance, a second red LED is sometimes used in combination with the first red LED to achieve more balanced light levels.

For either of the above two configurations of FIGS. 1 and 2, power is applied to the two LEDs in a manner such that only one of them is activated at any given time, so that, at any given time, the output signal from the detector is produced in response to light from at most one of these two LEDs. This simplifies calculations needed to convert detected light intensities into an indication of the oxygen concentration in a patient's blood.

The incompatibility between different types of probes and different types of oximeters significantly increases the cost of supplying probes for both types of oximeters. In particular, for the manufacturer of such probes, not only is there the cost of designing multiple different types of probes, there is also the cost of building multiple different manufacturing lines, purchasing components for multiple different manufacturing lines, sorting components for multiple different manufacturing lines and selling multiple different types of probes. In addition, the manufacturing and distribution costs of each different type of probe do not benefit as much from the economies of scale associated with the increased product volume that would occur if there were only one type of probe. The total cost of these probes also includes the indirect costs incurred by hospitals that use both types of probes so that such hospitals also bear the increased costs associated with the smaller volume orders of each type of probe, the cost of stocking multiple different types of probes and the costs of interacting with multiple vendors. All of these factors significantly increase the cost of monitoring patient oxygen saturation.

The Goldberger patent discussed above addresses this problem by presenting a probe that can be configured to work with any oximeter. The photodetector and light sources within this probe are mounted without any interconnections, and a cable interconnects these elements into various configurations by means of appropriately inserted jumper leads. Unfortunately, although this structure enables this probe to be adapted for a wide variety of oximeters, it does not allow any way for a probe which already has its electrical elements interconnected to be used with any arbitrarily selected oximeter.

It is an object of the invention to provide an adapter that can be connected between a probe that has its electrical elements interconnected in a first configuration and a monitor designed for use with a probe having a second electrical interconnect configuration such that this probe and this monitor will function properly with one another.

SUMMARY OF THE INVENTION

The present invention provides an adapter which actively connects a 2-lead oximeter probe or monitor to a 3-lead monitor or probe. This is done actively, with the alternating drive signals from the oximeter monitor providing a control signal for switching the adapter connections. The adapter connections are preferably made with diodes, transistors, or other active devices.

The adapter of the present invention thus first connects the 2 leads of the 2-lead device between the first and second terminals of the 3-lead device while a first light emitter is activated, and then connects the 2 leads between the second and third terminals of the 3-lead device. The 3-lead device can be either the oximeter monitor or the oximeter probe.

In one type of three-terminal monitor, only one of the two drive terminals (VO1, VO2) is active at a time, with the other drive terminal being in a high impedance state, and the third terminal connected to ground. In such a configuration, the adapter does not need to disconnect the other drive terminal. In another type of three-terminal monitor, the second drive terminal is not in a high impedance state. Thus, one adapter according to the present invention provides an extra switch to isolate this second drive terminal which is not being used. In one embodiment, this provides a four-transistor switch embodiment, rather than a two-transistor switch or two-diode embodiment.

In accordance with the illustrated preferred embodiments, two types of adapters are presented that are specially adapted to enable an oximeter probe to be utilized with an oximeter monitor with which it would otherwise be unable to be utilized. These two types of adapters are particularly useful because they enable two widely utilized types of oximeter probes to be utilized on both of their associated types of oximeter monitors.

The adapters in accordance with the invention are preferably either mounted on the monitor or in a cable used to connect a probe to a monitor, so that each adapter can become an extension of the oximeter itself and can be used by many different patients and can be used by each patient many times.

Several preferred adapter embodiments are specifically described for use with the two particular types of monitors and probes described below. However, the invention is applicable to any adapter which is to interconnect probes and monitors having differing numbers or configurations of light source signal connections.

The present invention also provides a dual-use probe which contains LEDs for both 3-lead and 2-lead type monitors. The LEDs are not interconnected inside the probe itself, allowing it to be dual-use since the interconnections can be done externally to provide the particular configuration required for the monitor being used. However, rather than duplicating all LEDs, only the IR LED is reproduced, with a common connector for all the LEDs allowing the red LED to be used for both types of monitors, with only one or the other of the IR LEDs being connected or used. Unlike the Goldberger patent, only three LED leads are required to allow the probe to be connected to either a 2-lead or 3-lead oximeter.

DESCRIPTION OF THE PREFERRED EMBODIMENT

Types of Monitors

3-Lead Other Monitor: This monitor is designed to drive a pair of LEDs that are connected in the 3-lead configuration, discussed above, in which:

the two LED anodes are connected to a common lead; and the two LED cathodes are each connected to its own, uniquely associated lead.

This type of monitor therefore has the following three terminals for coupling to this type of probe: a first terminal for coupling to the cathode of the first of these two LEDs; a second terminal for coupling to the cathode of the second of these two LEDs; and a third terminal for coupling to both anodes. As will be seen below, only two of these three terminals conduct electricity at any instant to the probe, a constraint that should be maintained when an adapter is used to interconnect a 2-lead probe to this type of monitor.

2-Lead Nellcor Monitor: In the second of these two types of oximeter monitors, the monitor is designed and adapted to drive a pair of LEDs connected in the 2-lead configuration in which:

the anode of a first LED and the cathode of a second LED are connected to a first lead; and the cathode of the first LED and the anode of the second LED are connected to a second lead.

This type of monitor therefore has the following two terminals for coupling to this type of probe: a first terminal for coupling to the first lead; and a second terminal for coupling to the second lead.

Alternatively, other types of probes may be used. In a variation of the 3 lead probe, the 2 LEDs may have the anode of one LED connected to the cathode of the other LED for the common (ground) terminal. In yet another alternative, the two cathodes could be connected to the common terminal, rather than the two anodes.

Types of Adapters

A first type of adapter is presented that enables a 3-lead oximeter monitor to drive an oximeter probe having a 2-lead configuration of two LEDs. This type of adapter will be referred to herein as a "3-to-2-Type Adapter".

A second type of adapter is also presented that enables a 2-lead oximeter monitor to drive an oximeter probe having a 3-lead configuration of two LEDs. This type of adapter will be referred to herein as a "2-to-3-Type Adapter". Thus, these two adapters enable each of these two types of oximeter monitors to be utilized with both of these two types of oximeter probes.

For each of these two types of adapters, the adapter can be mounted at a number of different points in the electrical path from the monitor to the probe. In particular, it can be mounted: within the monitor, externally on a front panel of the monitor, within the cable connecting the probe to the monitor, in the connector at the monitor end of the cable, or at the connector to the probe.

These 2 types of adapters must each function to: (1) convert LED drive signals, from one type of monitor, to the type of LED drive signals expected by a probe designed to operate with the other type of monitor; and (2) transmit data from this probe back to the monitor in a format expected by the monitor.

In order to convert LED drive signals of the form produced by one of these types of monitors into LED drive signals of the form produced by the other of these types of monitors, it is necessary to selectively redirect portions of the input signals received from the monitor. This is achieved by using the LED drive signals produced by the monitor in a dual role of providing power to the LEDs in the probe and also providing timing data for controlling the adapter to produce the desired output signals. The preferred embodiments of the adapters presented herein use active switching to adapt the LED drive signals into signals applied to the LEDs.

In a preferred embodiment, the adapter has the form of a double-pole, double-throw (DPDT) switch, that is actively switched in response to at least one of the LED drive signals from the monitor. However, a 3-to-2-type adapter can be implemented by any structure that converts a pair of LED drive signals VO1 and VO2 into a pair of LED drive signals VN1 and VN2. Likewise, a 2-to-3-type adapter can be implemented by any structure that converts a pair of LED drive signals VN1 and VN2 into a pair of LED drive signals VO1 and VO2.

A 3-to-2-type adapter must convert LED drive signals from a 3-lead monitor into LED drive signals required by a 2-lead probe and a 2-to-3-type adapter must convert LED drive signals from a 2-lead monitor into LED drive signals required by a 3-lead probe. The following two sections describe particular examples of these two sets of probes, monitors, and signals.

Operation of a 3-Lead Monitor with a 3-Lead Probe

A 3-lead monitor 51 provides, at a first terminal, a signal VO1 (illustrated in FIGS. 1 and 4) that can be no signal, with the terminal switched into an open state (i.e., high impedance state) or can be driven to a negative voltage. A second terminal provides a signal VO2 (also illustrated in FIGS. 1 and 4) that can be no signal with the terminal switched into an open state (i.e., high impedance state) or can be driven to a negative voltage. A return common ground GND at a third terminal is also provided. This monitor is intended to be utilized with a 3-lead probe, with the return common ground connected to the anodes of the LEDs 11, 12 illustrated in FIG. 1. Alternately, the common terminal could be connected to a positive voltage, with the other terminals alternately grounded.

LED 12 emits light when VO1 is negative and LED 11 emits light when VO2 is negative. VO1 and VO2 are intentionally never negative at the same time, so that only one or none of LEDs 11 and 12 is activated at any given time. This ensures that a patient is exposed to only one wavelength of light at a time, so that the photodetector receives optical signals for at most a single wavelength of light at any given time. This simplifies analyzing the spectral data contained in the light received by photodetector 17. Optionally, a dark signal is also measured when both LEDs are off.

Operation of a 2-Lead Monitor with a 2-Lead Probe

Figure 3:
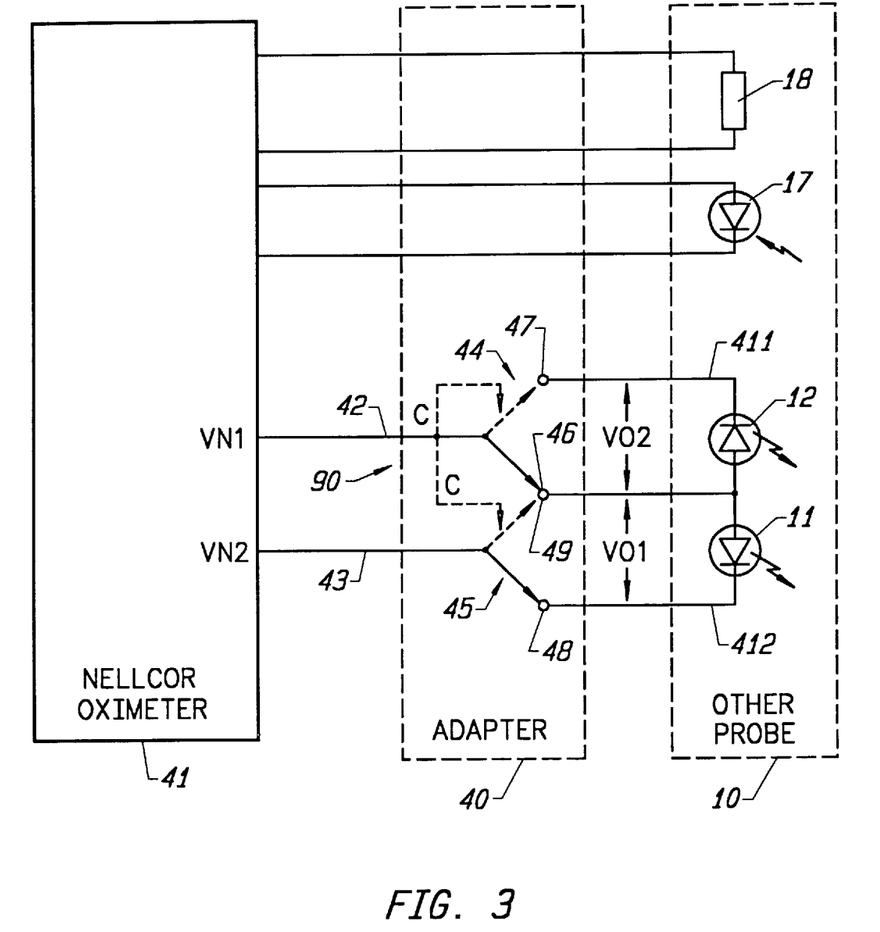
FIG. 3 illustrates the use of a double-pole, double-throw switch as a 2-to-3 Type Adapter for connecting a 2-lead monitor to a 3-lead probe.

In a 2-lead monitor 41, a first terminal provides a signal VN1 (illustrated in FIGS. 2 and 3) and a second terminal provides a signal VN2 (also illustrated in FIGS. 2 and 3). This monitor is intended to be utilized with a 2-lead probe.

LED 21 emits light when VN1 is high and VN2 is low. LED 22 emits light when VN2 is high and VN1 is low. Neither LED is on if either of the lines for these two signals is open (in a high impedance state). Because VN1 and VN2 are applied to opposite ends of both LEDs, if VN1 and VN2 are both equally high or are both equally low at the same time, a net zero voltage drop is produced across both LEDs and therefore both LEDs are also off in such intervals. The current through the LEDs is typically limited by limiting circuits in the LED drivers in the monitor.

General Structure of the Adapters

A 3-to-2-type adapter can take any structural form that enables the signals VN1 and VN2 (illustrated in FIG. 2) to be generated in response to input signals VO1 and VO2 (illustrated in FIG. 1).

According to a preferred embodiment the adapters can each be implemented in the form of a double-pole, double-throw switch (hereinafter referred to as a "DPDT switch"), that is switched in response to one or both of the signals provided by the monitor. Thus, such signals from the oximeter monitor are utilized in a dual manner: to provide power to an associated LED; and to control switching of the adapter. The LED drive current can be varied by the oximeter to achieve the desired light levels at the detector. The switches must be chosen so that they will operate over the entire range of possible current levels.

2-to-3-Type Adapter

FIG. 3 illustrates the use of a double-pole, double-throw (DPDT) switch 90 as a 2-to-3 Type Adapter for connecting a 2-lead monitor 41 to a 3-lead probe 10. Input signal VN1 is applied to a first input lead 42 of DPDT switch 90 and input signal VN2 is applied to a second input lead 43 of DPDT switch 90. The operation of this DPDT switch is most easily understood by viewing this switch as a pair of single-pole, double throw (SPDT) switches 44 and 45 having input leads 42, 43 and output leads 46–49. Output leads 46 and 49 are shorted together and are to be connected to the common anode terminal 410 of diodes 11 and 12. Output lead 47 is connected to the cathode 411 of LED 12 and output lead 48 is connected to the cathode 412 of LED 11.

A control signal C controls the states of the SPDT switches such that the switches are either in: a first state in which only LED 11 is activated or in a second state in which only LED 12 is activated. This first state is illustrated by the solid line positions of SPDT switches 44 and 45 and the second state is illustrated by the dashed line positions of SPDT switches 44 and 45. In an alternate embodiment, the control signal C could be from lead 43.

In this first state, input lead 42 which is positive, is connected through output lead 46 to the common anode 410, and input lead 43 which is now negative is connected through output lead 48 to the cathode 412 of LED 11, thereby turning on only LED 11. In this second state, input lead 42 which is now negative is connected through output lead 47 to the cathode 411 of LED 12, and input lead 43 which is now positive is connected through output lead 49 to common anode 410 thereby turning on only LED 12. The resulting signal pattern produced across LED 11 is therefore substantially identical to VO1 and the resulting signal pattern produced across LED 12 is therefore substantially identical to VO2.

3-to-2-Type Adapter

Figure 4:
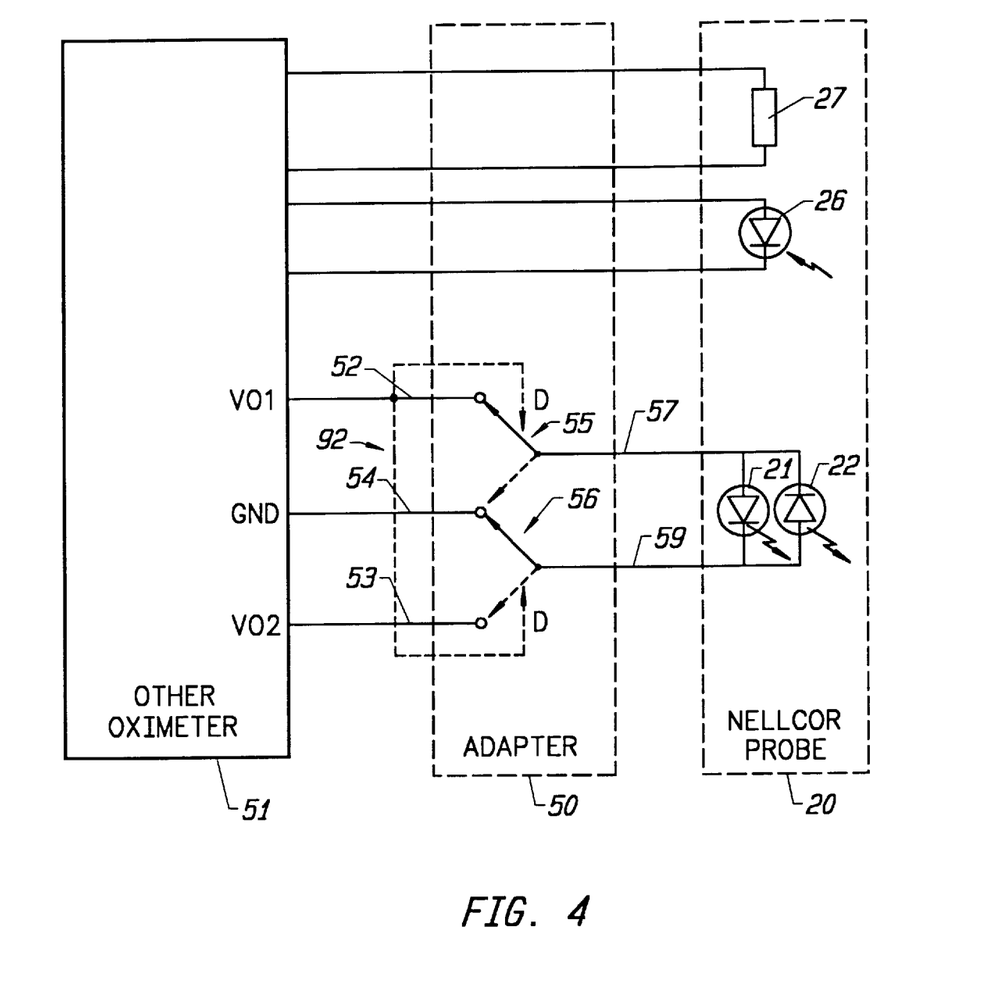
FIG. 4 illustrates the use of a double-pole, double-throw switch as a 3-to-2 Type Adapter for connecting a 3-lead monitor to a 2-lead probe.

FIG. 4 illustrates an embodiment of a 3-to-2-type adapter that utilizes a double-pole, double-throw (DPDT) switch to enable input signals VO1 and VO2 to drive a 2-lead probe 20.

In FIG. 4, a double-pole, double-throw switch 92 functions as a 3-to-2-type adapter to connect a 3-lead monitor 51 to a 2-lead probe 20. Input signal VO1 is applied to a first input lead 52 of DPDT switch 92, input signal VO2 is applied to a second input lead 53 of DPDT switch 92 and a ground GND of the monitor is connected to a third (common) input lead 54 of DPDT switch 92.

A control signal D (which in this embodiment is derived from VO1) controls the state of the DPDT switch. The operation of this DPDT switch can be understood in terms of its equivalence to a pair of single-pole, double-throw switches 55 and 56. In a first state (illustrated by the solid line positions of SPDT switches 55 and 56), which occurs when VO1 is negative and VO2 is off, VO1 is applied to a first output lead 57 that is connected to a first input lead 58 of probe 20 and ground GND is connected to a second output lead 59 that is connected to a second input lead 510 of probe 20, thereby turning on only LED 22.

In a second state (illustrated by the dashed line positions of SPDT switches 55 and 56), which occurs when VO1 is off and VO2 is negative, VO2 is applied to output lead 59 and ground GND is connected to output lead 57, thereby turning on only LED 21. The resulting signal pattern produced across LED 21 is therefore substantially identical to VN1 and the resulting signal pattern produced across LED 22 is therefore substantially identical to VN2.

Packaging

Adapters 40, 50 can be packaged into an oximeter system in a number of different ways. Either of these adapters can be: included within the monitor; mounted on a front panel of the monitor such that it can be connected to the appropriate leads from the monitor; included in the cable that connects the probe to the monitor (in a housing spliced withing the length of the cable); mounted at an input end of the probe such that it can be connected to appropriate leads from the probe; mounted in the cable connector to the monitor or to the probe; or included within the probe. It is preferred to have the adapter detachably connected to the cable and/or the monitor so that a user can utilize such adapter with existing types of cables and monitors to enable each of the above-discussed types of probes to be utilized with the other type of monitor.

Preferred Embodiments

Figure 5:
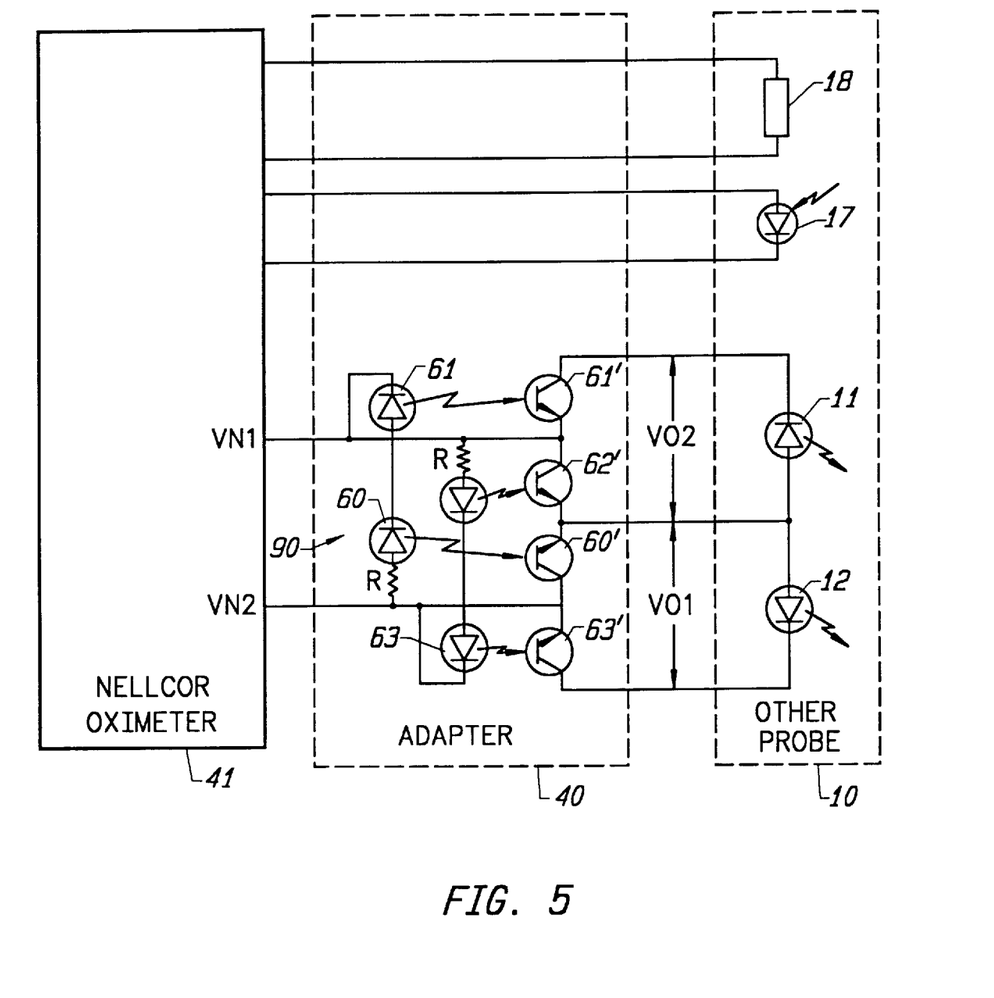
FIG. 5 illustrates a first preferred embodiment of a 2-to-3 Type Adapter.

FIG. 5 illustrates one preferred embodiment of a 2-to-3 Type Adapter 40, corresponding to the adapter presented in FIG. 3. This adapter enables a a 2-lead monitor 41 to drive a 3-lead probe 10. This adapter contains a DPDT switch 90 consisting of LEDs 60–63 with corresponding phototransistors 60'–63'. The optical coupling does not require external power separate from the current provided by the monitor for the LEDs for this DPDT switch to operate. It is important to keep the current to the optical switches low by using resistors R because the adapter drains some of the current provided by the input signals VN1 and VN2, thereby reducing the amount of current applied to the probe LEDs 11 and 12.

When VN1 is high and VN2 is low (the first state of DPDT switch 90), LEDs 62 and 63 emit light to photodiodes 62' and 63', respectively, thereby connecting signal VN2 through photodiode 63', LED 12 and photodiode 62' to VN1. This turns LED 12 on. However, because LEDs 60 and 61 are reverse biased, the associated photodiodes 60' and 61' are in an off state so that LED 11 is off.

When VN1 is low and VN2 is high (the second state of DPDT switch 40), LEDs 60 and 61 emit light to photodiodes 60' and 61', respectively, thereby connecting signal VN1 through photodiode 61', LED 11 and photodiode 60' to VN2. This turns LED 11 on. However, because LEDs 62 and 63 are reverse biased, the associated photodiodes 62' and 63' are in an off state so that LED 12 is off.

Figure 6:
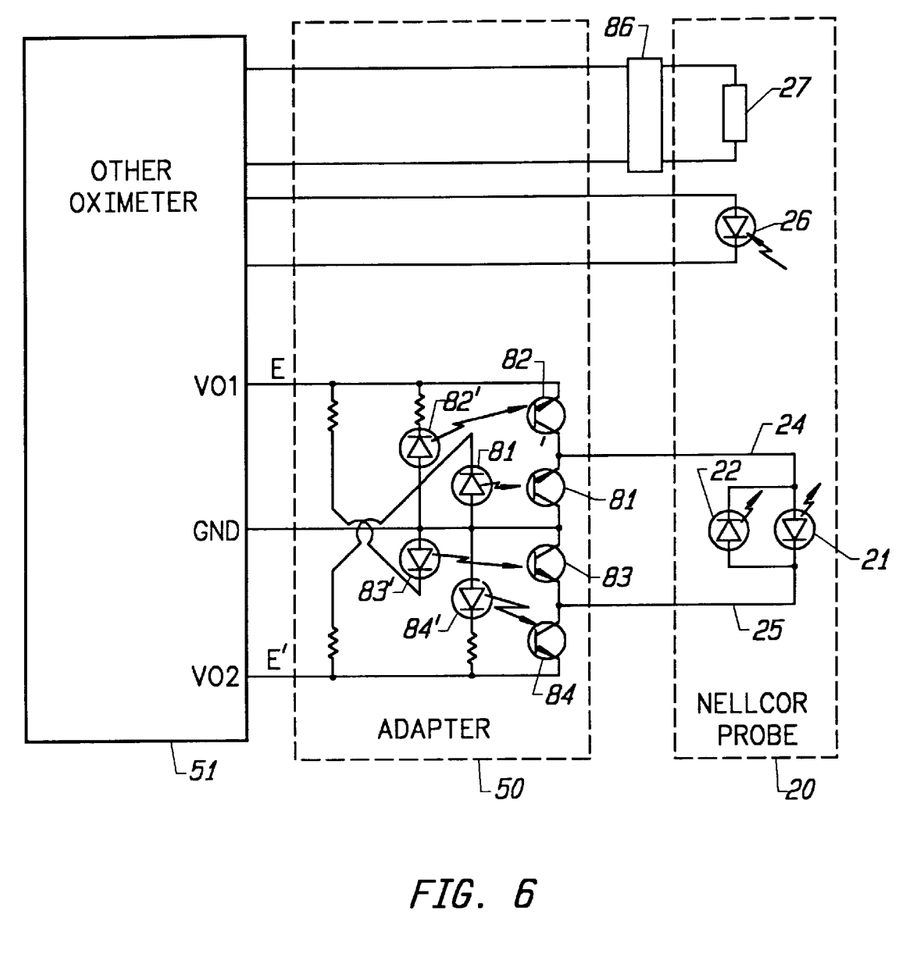
FIG. 6 illustrates a first preferred embodiment of a 3-to-2 Type Adapter.

FIG. 6 illustrates a first preferred embodiment of a 3-to-2 Type Adapter that utilizes a set of four optically isolated switches with switching transistors 81–84 and control LEDs 81'–84'. The resistive current limiting on the switch inputs (LEDs 81'–84') again minimizes power consumption for active switching. These optically-coupled embodiments typically pass 80–90% of the power in the input signals to the output signals from the adapter. VO1 functions as an input signal that is selectively gated to the probe and also functions as a first control signal E. VO2 likewise functions as an input signal that is selectively gated to the probe and also functions as a second control signal E'. Switches 81 and 84 are conductive only when VO2 is negative and switches 82 and 83 are conductive only when VO1 is negative. When VO1 and VO2 are both at zero volts, all the switches 81–84 are nonconductive and neither of LEDs 21 and 22 is turned on. When VO1 is negative and VO2 is at zero volts, only switches 82 and 83 are turned on. This applies VO1, through switch 82 to lead 24 (making it negative), thereby turning LED 22 on through 83 to ground GND and turning LED 21 off. When VO1 is at zero volts and VO2 is negative, only switches 81 and 84 are turned on. This applies VO2 through switch 84 to lead 25 (making it negative), thereby turning LED 21 on through 81 to ground GND and turning LED 22 off. VO1 and VO2 are never both low simultaneously, so there are only three distinct states: only LED 21 on; only LED 22 on; or both LED 21 and LED 22 off.

The embodiment of FIG. 6 could be modified to eliminate transistors 82 and 84 (and the corresponding LEDs, 81'–84'), providing direct connections instead. Transistors 82 and 84 serve to isolate VO1 or VO2 when it is not being used, and this is not necessary if the lines for VO1 and VO2 are at a high-impedance state when not being activated. An embodiment which would work with an output that is high impedance is shown in FIG. 8, described below.

FIG. 6 also shows an external coding element 86 which can be added in parallel (or alternately in series) with coding resistor 27 to modify its value to a value expected by a different type of monitor (element 86 can be a resistor or some other active or passive element). This is useful because different monitors use different resistor values for the same wavelength. This could be added to any of the probes or adapters shown, not just the embodiment of FIG. 6.

Figure 7:
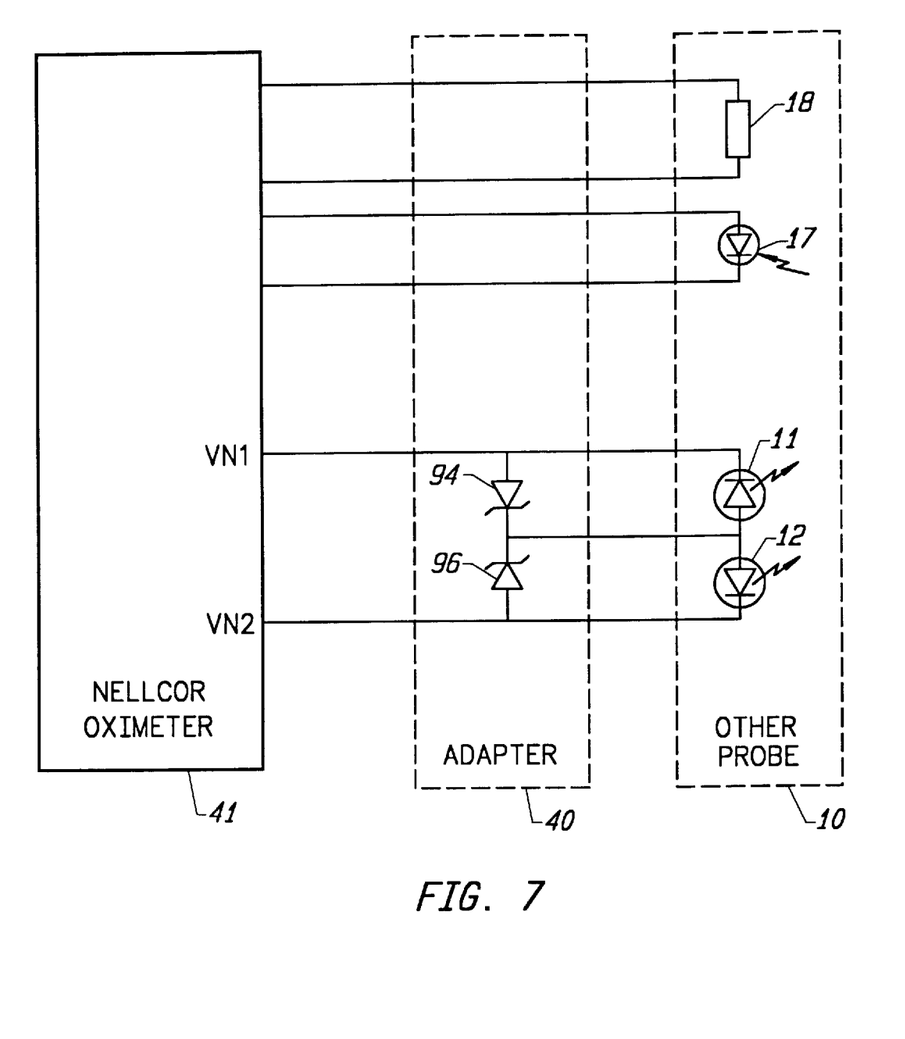
FIG. 7 illustrates a second preferred embodiment of a 2-to-3 Type Adapter.

FIG. 7 illustrates a second preferred embodiment of a 2-to-3 Type Adapter 40. This adapter uses two Schottky diodes 94 and 96. When VN1 is high, current will flow through Schottky diode 94 to the common node and through LED 12 back to the VN2 lead, which is low at this time. LED 11 will be reverse biased, and will not conduct, and neither will the Schottky diode 96. When VN2 is high, current will flow through Schottky diode 96 and LED 11, returning to VN1, which is low at this time. Here, LED 12 and Schottky diode 94 are reverse biased, with neither of them conducting. Schottky diodes are preferred over normal diodes since they have lower forward voltage drops.

Figure 8:
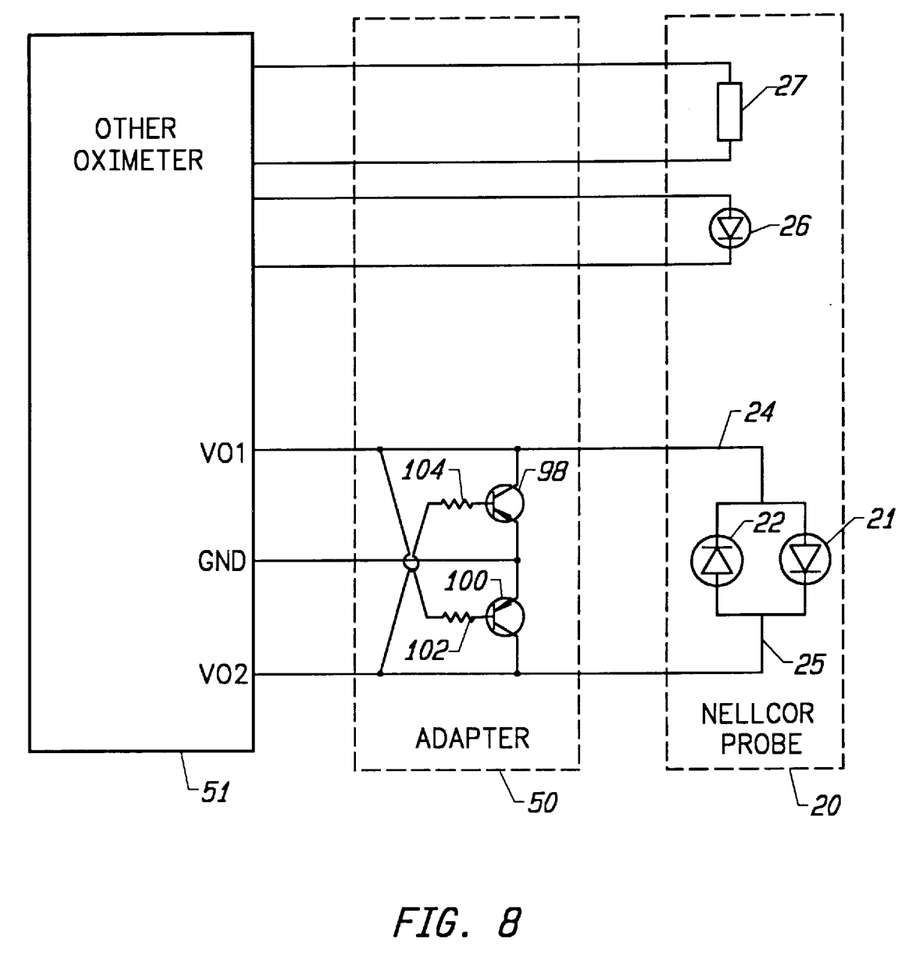
FIG. 8 illustrates a second preferred embodiment of a 3-to-2 Type Adapter for use with a high impedance output oximeter monitor.

FIG. 8 illustrates a second preferred embodiment of a 3-to-2 Type Adapter 50. This adapter includes two transistors 98 and 100. The VO1 terminal is connected through a resistor 102 to the base of transistor 100. The VO2 signal is connected through a resistor 104 to the base of transistor 98. Both the transistors are PNP type transistors and thus will turn on when the base is low compared to their emitter. The emitters are connected to the ground terminal.

In use, VO1 or VO2 becomes negative with respect to ground. When VO1 becomes negative, that turns on transistor 100, forming a path between ground and terminal 25 of the probe 20. Thus, current will flow from ground through transistor 100 through LED 22, which is turned on, and return to VO1. With VO2 in a high impedance state, the base of transistor 98 will be negative by only the amount of the collector to emitter voltage drop of transistor 100, which will be insufficient to turn on transistor 98.

Alternately, when VO2 goes negative with respect to ground, transistor 100 will turn off (because VO1 is in a high impedance) and transistor 98 will turn on. Thus, current will flow from ground, through transistor 98, through LED 21 and return to VO2. The resistors are used to limit the amount of current drawn to activate transistors 98 and 100. This embodiment assumes VO1 and VO2 are in a high impedance state when inactive, and thus another set of switches for isolation is not needed.

As can be seen from the above descriptions, the present invention "steals" power (current) from the monitor's LED drive current in order to perform a function not performed within the pulse oximeter monitor. In particular, the function performed in a preferred embodiment is controlling the switching of connections. This is particularly true in the embodiments of FIGS. 5, 6 and 8, in which power is used to control the switches. The power not "stolen" is used to drive the probe LEDs. As shown in particular in FIGS. 6 and 8, resistors can be used to limit the amount of current diverted.

Figure 9:
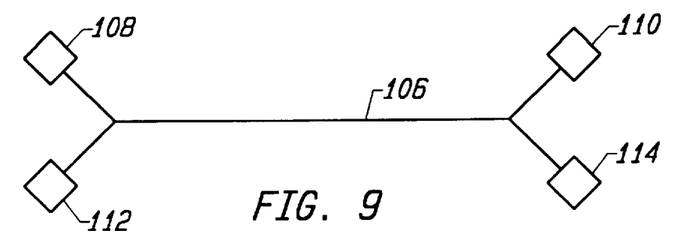
FIG. 9 illustrates a combined adapter cable.

FIG. 9 illustrates an embodiment of the present invention which may be incorporated into a cable for interconnecting a probe to an oximeter monitor. FIG. 9 shows a cable 106 with a monitor connector 108 for connecting to a 3-lead monitor, and a probe connector 110 for connecting to a 3-lead probe. Similarly, a connector 112 for connecting to a 2-lead monitor is provided, along with a connector 114 for connecting to a 2-lead probe. The use of such a universal cable would allow any type of monitor to be connected to any type of probe, eliminating the need to stock multiple types of adapters.

Figure 10:
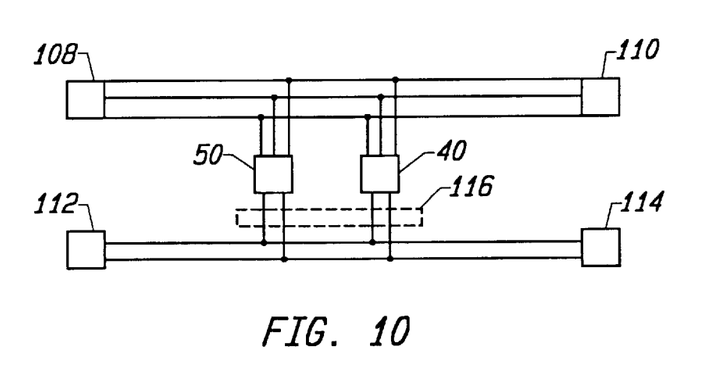
FIG. 10 illustrates the multiple adapter connections in the cable of FIG. 9 for a combined adapter.

FIG. 10 shows the interconnections of the connector of FIG. 9, with an adapter 50 interconnecting the 3-lead oximeter connector 108 to the 2-lead probe connector 114. Similarly, adapter 40 interconnects the 2-lead oximeter monitor connector 112 to the 3-lead probe connector 110. This cable can be operated so that the connections not used are simply left open, providing an open circuit (high impedance) that would not affect the operation of the other adapter. Alternately, a mode switch 116 could be added to actively disconnect the adapter which is not being used to prevent any possible power drain through its components while the other adapter is being used. The adapters 50, 40 and mode switch 116 would be preferably formed as a part of cable 106 or connected thereto.

Figure 11:
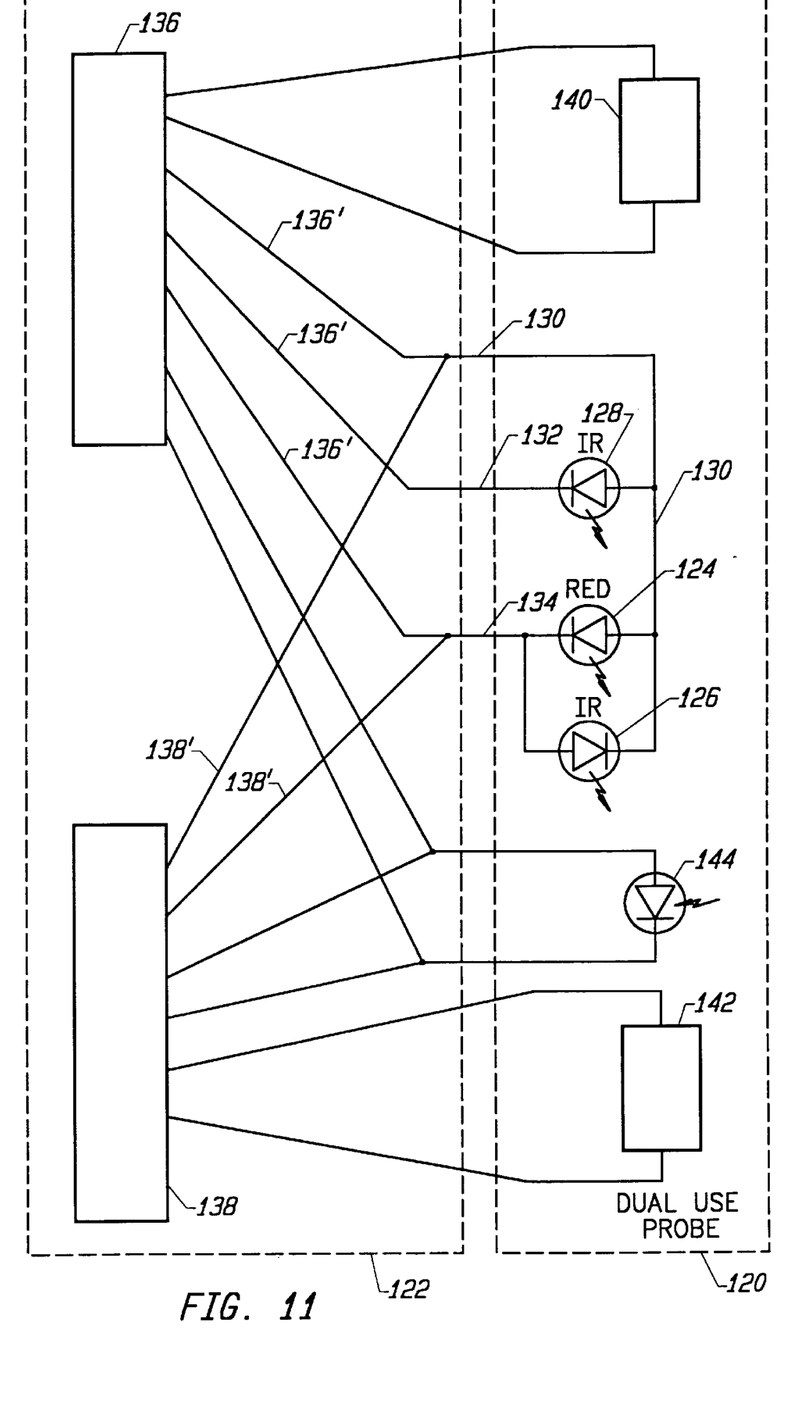
FIG. 11 illustrates a preferred embodiment of a dual use probe and corresponding adapter.

FIG. 11 is a diagram showing a dual use probe 120 and a corresponding adapter 122. Alternately, these could be combined in a single unit. In yet another alternative, the adapter could be eliminated and the probe 120 could be directly connected to either a two LED drive monitor or a 3 LED drive monitor. The dual use probe contains an 2-lead arrangement of LEDs 124 and 126. In this instance, LED 124 is preferably in the red wavelength band, and LED 126 is in the IR wavelength band. An additional LED 128 is added, corresponding to the second LED of the 3-lead arrangement. Three output terminals are provided, an output terminal 130 which is common to all the LEDs, a terminal 132 from the cathode of LED 128, and a terminal 134 from the cathode of LED 124, also connected to the anode of LED 126. In this configuration, the LEDs necessary for either type of probe, 10 or 20, are provided.

Adapter 122 shows two different connectors, a connector 136 for a 3-lead monitor, and a connector 138 for a 2-lead monitor. For the 2-lead connector 138, only leads 130 and 134 of dual use probe 120 are used. On the other hand, for 3-lead connector 136, all three leads 130, 132, and 134 are utilized.

Lines 138' show how the 2 LED drive connector 138 is connected to alternately drive LEDs 124, 126, and lines 136' show how the 3 LED drive connector 136 is connected to alternately drive LEDs 126, 128. The drive interconnections can thus be made externally to the probe, thus making the probe equally applicable to either type of monitor.

As can be seen, when connector 138 is connected to a 2-lead monitor, only leads 130, 134 are utilized, with 132 being open. Since lead 132 is open, LED 128 is effectively taken out of the circuit, and the probe and monitor can operate in the normal manner using LEDs 124 and 126.

When connector 136 for a 3-lead type monitor is used, all three leads are used. However, LED 126 is effectively taken out of the circuit since current never flows in a direction which would activate it. In a first mode, lead 130, which is connected to ground, provides current to a negatively-biased lead 132 through IR LED 128. At this point, lead 134 is high impedance, and no current flows in this direction. In the second mode, lead 130 is again ground, with lead 132 being at a high impedance and lead 134 being pulled negative. This causes current to flow through red LED 124, but not through LED 126, which is reverse biased.

Two different IR LEDs are used rather than two different red LEDs, since oximeter probes currently on the market will typically have red LEDs of approximately the same wavelength, while their IR LEDs differ.

In addition, dual use probe 120 contains two coding elements (active or passive), 140 and 142. Coding element 140 is used to indicate the wavelength of red LED 124 (and/or other significant parameters) to a 3-lead type oximeter monitor connected to connector 136. A separate coding element 142 is used to indicate the wavelength of the red LED 124 (and/or other significant parameters) for a 2-lead monitor. Although the red LED will have the same wavelength, alternate coding schemes are used for monitors currently in the market for the same wavelengths. Accordingly, the leads of element 140 are only connected to connector 136, and the leads of element 142 are only connected to connector 138. The detector 144 is connected to both connectors.

Though the invention has been described with reference to certain preferred embodiments thereof, it is not to be limited thereby. Any one of a variety of active switches are well known in the art and could readily be substituted for the double pole double throw switches described herein. In addition, numerous electronic elements other than the phototransistors and transistors described herein could be utilized to effectuate the electronic switching. For example, a light emitter other than a LED could be used, with its terminals broadly referred to as an emitter drive terminal and an emitter output terminal, rather than an anode and cathode. Alternatively, the adapter could be designed to allow the 2-lead portion of the adapter to connect to either a 2-lead oximeter or a 2-lead probe, rather than being specialized to just one of these orientations. Similarly, the 3-lead portion of the adapter could connect to either a 3-lead monitor or a 3-lead probe. All such equivalents are encompassed by the invention, the invention only being limited by the appended claims.

What is claimed is:

1. An adapter for enabling a first type of optical oximeter probe to be utilized with an oximeter monitor that provides probe signals for use with a second type of optical oximeter probe, said adapter comprising:

(a) a set of N signal inputs for receiving N input signals from an oximeter monitor for powering at least one light emitter;

(b) a set of M signal outputs for providing M output signals to an oximeter probe having said at least one light emitter configured to connect to M signal inputs, wherein M and N are different integers each of which is greater than 1;

(c) an active switch which actively connects said N inputs to said M outputs, thereby actively gating;

wherein at least one of the input signals functions as a control signal to actively control gating of said input signals.

2. An adapter as in claim 1 wherein said active switch gates preselected portions of at least one of the input signals to produce the output signals.

3. An adapter as in claim 1 wherein said active switch gates to said outputs preselected portions of at least two input signals.

4. An adapter as in claim 1 wherein said active switch comprises at least one optically-coupled switch, thereby reducing a fraction of power provided by said input signals that must be diverted away from output signals in order to provide power for changing states of said active switch, thereby increasing a fraction of this power that is transferred to said optical oximeter probe.

5. An adapter as in claim 1 wherein only one of the input signals functions as a control signal.

6. An adapter as in claim 1 wherein N equals 2 and wherein each of the two input signals functions as a control signal that controls gating of the input signals through said adapter.

7. An adapter as in claim 1 wherein said adapter is fixedly secured to said monitor.

8. An adapter as in claim 1 wherein said adapter is incorporated into a cable that releasably connects to said probe and which connects to said monitor.

9. An adapter as in claim 1 wherein said adapter is incorporated into one of: said probe, a cable nonreleasably connected to said probe, or a cable connector formed at an end of a cable which is nonreleasably connected to said probe.

10. An adapter as in claim 1 wherein said active switch is a double-pole, double-throw (DPDT) switch.

11. An adapter as in claim 10, wherein said DPDT switch is a 2-to-3 type switch for use with a probe having a pair of LEDs connected in a 3-lead configuration, said DPDT switch comprises:

a first SPDT switch having (i) an input for receiving a first input signal (VN1), (ii) a first output for connection to a first lead of a 3-lead probe, and (iii) a second output for connection to a second lead of said 3-lead probe; and a second SPDT switch having (i) an input for receiving a second input signal (VN2), (ii) a first output for connection to said second lead of said 3-lead probe, and (iii) a second output for connection to a third lead of said 3-lead probe.

12. An adapter as in claim 11 wherein both SPDT switches are controlled by the signal applied to the input of the 1st SPDT switch.

13. An adapter for enabling a first type of optical oximeter probe to be utilized with an oximeter monitor that provides probe signals for use with a second type of optical oximeter probe, said adapter comprising:

(a) a set of N signal inputs for receiving N input signals from an oximeter monitor for powering at least one light emitter;

(b) a set of M signal outputs for providing M output signals to an oximeter probe having said at least one light emitter configured to connect to M signal inputs, wherein M and N are different integers each of which is treater than 1;

(c) an active switch which actively connects said N inputs to said M outputs, thereby actively gating;

wherein said active switch is a double-pole, double-throw (DPDT) 3-to-2-type switch comprising:

a first SPDT switch having (i) a first input receiving a first input signal (VO1), (ii) a second input connected to system monitor ground (GND) and an output for connection to a first input lead of a probe;

a second SPDT switch having (i) a first input receiving a second input signal (VO2), (ii) a second input connected to system monitor ground (GND), and an output for connection to a second input lead of said probe.

14. An adapter as in claim 13 wherein said first SPDT switch is controlled by a signal applied to an input of said first SPDT switch.

15. An adapter for enabling a first type of optical oximeter probe to be utilized with an oximeter monitor that provides probe signals for use with a second type of optical oximeter probe, said adapter comprising:

(a) a set of N signal inputs for receiving N input signals from an oximeter monitor for powering at least one light emitter;

(b) a set of M signal outputs for providing M output signals to an oximeter probe having said at least one light emitter configured to connect to M signal inputs, wherein M and N are different integers each of which is greater than 1;

(c) an active switch which actively connects said N inputs to said M outputs, thereby actively gating, wherein said active switch is a 3-to-2-type switch comprising:

a first input, selectively connected to a first output, for receiving a first input signal (VO1);

a second input, selectively connected to a second output, for receiving a second input signal (VO2);

a third input; and a SPDT switch having an input connected to a ground line (GND) and having a pair of outputs for connecting to either of said first and second outputs.

16. An adapter as in claim 15 wherein said active switch is controlled by a signal applied to said first input.

17. The adapter of claim 15 wherein said third input is connected to said ground line.

18. An adapter for connecting an optical oximeter to a probe, said probe having at least first and second light emitters, said adapter comprising:

a common terminal for connecting to a one of said probe and said oximeter which is a three terminal device, the other being a two terminal device;

at least a first light emitter drive terminal for connecting to said oximeter for providing an activating signal for one of said light emitters; and a switching circuit, responsive to said activating signal, for alternately connecting, coincident with the alternate activation of said light emitters, said common terminal to two different I/O terminals of the two terminal device.

19. The adapter of claim 18 wherein said common terminal is for connecting to said probe, and said two different I/O terminals are for connecting to said oximeter, one of said two different I/O terminals being said first light emitter drive terminal, the other being a second light emitter drive terminal, said adapter having first and second probe terminals for coupling to said first and second light emitters of said probe.

20. The adapter of claim 19 wherein said switching circuit comprises:

a first transistor or a first diode coupled between said first light emitter drive terminal and said common terminal; and a second transistor or a second diode coupled between said second light emitter drive terminal and said common terminal.

21. The adapter of claim 20 further comprising:

a third transistor or diode coupled between said first light emitter drive terminal and said first probe terminal; and a fourth transistor or diode coupled between said second light emitter drive terminal and said second probe terminal.

22. The adapter of claim 20 wherein said first and second transistors or diodes are optically activated.

23. The adapter of claim 18 wherein said common terminal is for connecting to said oximeter, and said two different terminals are for connecting to said probe.

24. The adapter of claim 23 wherein said switching circuit comprises:

a first transistor or a first diode coupled between a first probe terminal and said common terminal; and a second transistor or a second diode coupled between a second probe terminal and said common terminal.

25. The adapter of claim 24 further comprising:

a third transistor or diode coupled between a first light emitter drive terminal and said first probe terminal; and a fourth transistor or diode coupled between a second light emitter drive terminal and said second probe terminal.

26. The adapter of claim 18 further comprising:

a second light emitter drive terminal for connecting to said oximeter, said switching circuit being responsive to activating signals on both said first and second light emitter drive terminals.

27. The adapter of claim 18 wherein said switching circuit includes one of a diode and a transistor.

28. The adapter of claim 18 wherein said switching circuit includes at least one optically isolated switch.

29. The adapter of claim 18 wherein said switching circuit draws less than 20 percent of the power of said activating signal.

30. An adapter for connecting an optical oximeter to a probe, said probe having at least first and second light emitters, said adapter comprising:

a common terminal for connecting to a one of said probe and said oximeter which is a three terminal device;

a first light emitter drive terminal for connecting to said oximeter for providing a first activating signal for said first light emitter;

a second light emitter drive terminal for connecting to said oximeter for providing a second activating signal for said second light emitter;

a first probe terminal for connecting to at least one of said light emitters in said probe;

a second probe terminal for connecting to at least one of said light emitters in said probe;

a switching circuit, responsive to both said first and second activating signals, for alternately connecting, coincident with the alternate activation of said light emitters, said common terminal to either said first and second light emitter drive terminals or said first and second probe terminals.

31. The adapter of claim 30 wherein said first light emitter drive terminal is connected to said first probe terminal and said second light emitter drive terminal is connected to said second probe terminal.

\* \* \* \* \*